United States Patent [19]

Nelson et al.

[11] Patent Number: 5,613,954
[45] Date of Patent: Mar. 25, 1997

[54] LAPAROSCOPIC SURGICAL Y-TUBE CANNULA

[75] Inventors: Charles L. Nelson, Pleasanton; John Nguyen, San Jose; Derrick A. Richardson, Fremont; Heber Saravia, San Francisco, all of Calif.

[73] Assignee: Stryker Corporation, Kalamazoo, Mich.

[21] Appl. No.: 342,926

[22] Filed: Nov. 21, 1994

[51] Int. Cl.⁶ .................................................. A61M 5/178
[52] U.S. Cl. .......................... 604/167; 604/905; 604/286
[58] Field of Search ................................ 604/247, 248, 604/256, 167, 175, 35, 158, 181, 264, 284, 283, 905

[56] References Cited

U.S. PATENT DOCUMENTS

| | | | |
|---|---|---|---|
| 4,424,833 | 1/1984 | Spector et al. | 604/167 |
| 4,655,752 | 4/1987 | Honkanen et al. | 604/256 |
| 4,886,507 | 12/1989 | Patton et al. | |
| 4,917,668 | 4/1990 | Haindl | 604/167 |
| 5,006,114 | 4/1991 | Rogers et al. | 604/167 |
| 5,167,636 | 12/1992 | Clement. | |
| 5,201,714 | 4/1993 | Gentelia et al. | |
| 5,269,763 | 12/1993 | Boehmer et al. | |
| 5,273,545 | 12/1993 | Hunt et al. | |
| 5,312,362 | 5/1994 | Pfolsgraf et al. | |
| 5,352,215 | 10/1994 | Thome et al. | 604/283 |
| 5,458,640 | 10/1995 | Gerrone | 604/264 |

Primary Examiner—Robert A. Hafer
Assistant Examiner—Justine Yu
Attorney, Agent, or Firm—Flynn, Thiel, Boutell & Tanis, P.C.

[57] ABSTRACT

A laparoscopy cannula having an acutely angled suction irrigation branch, incorporating a suction irrigation fluid seal which is accessible for replacement and a cooperating rotatable and axially slidable coupling having an internal portion for connection to and support of a suction irrigation handpiece.

17 Claims, 5 Drawing Sheets

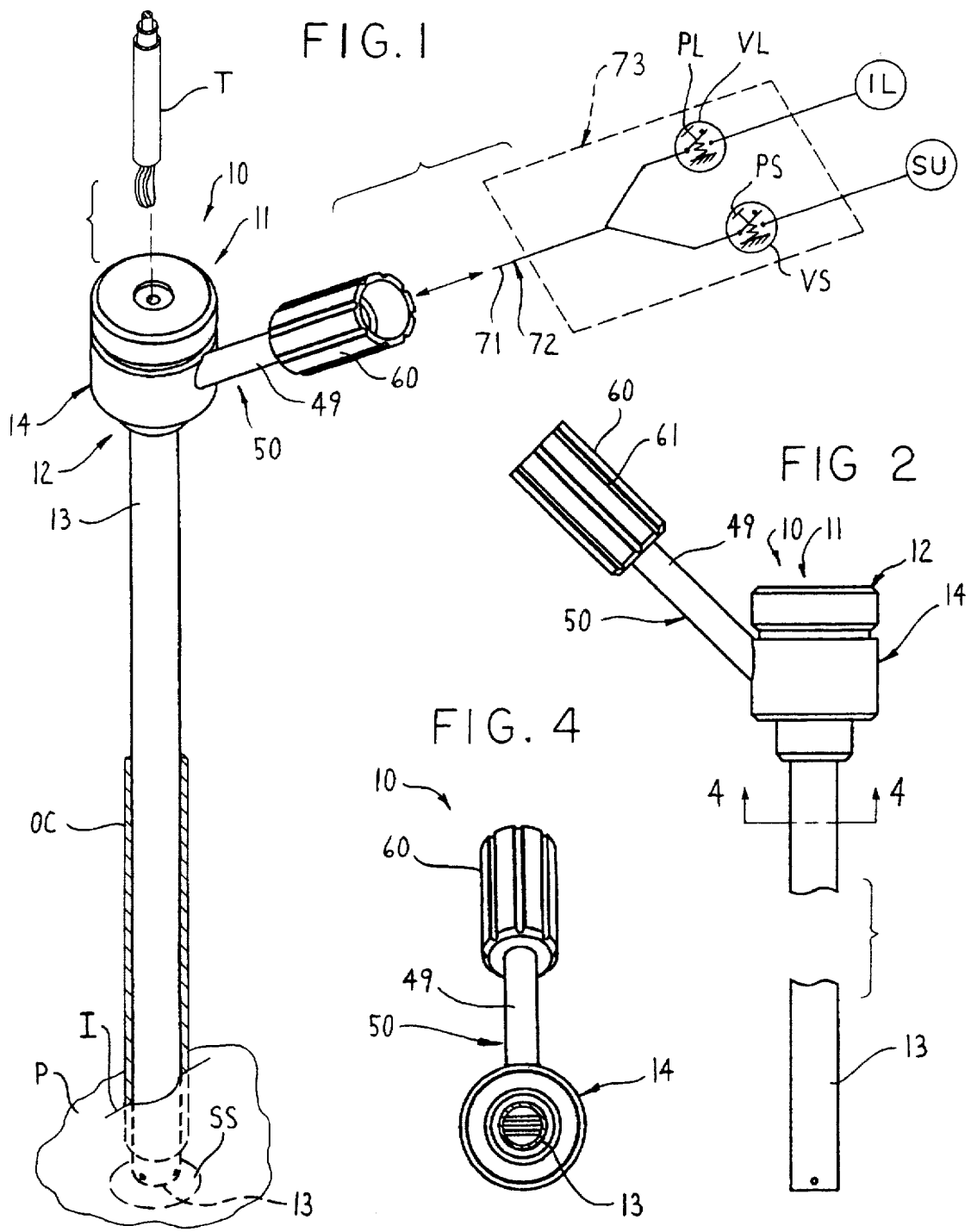

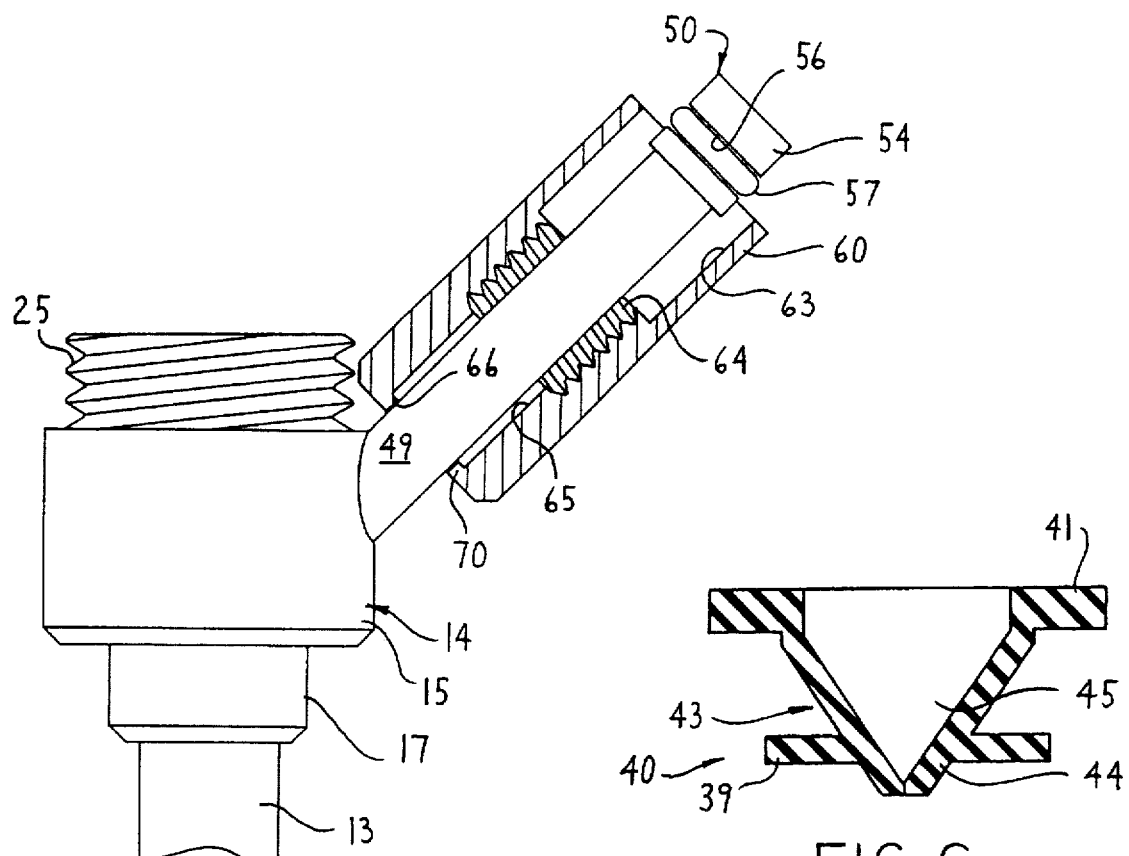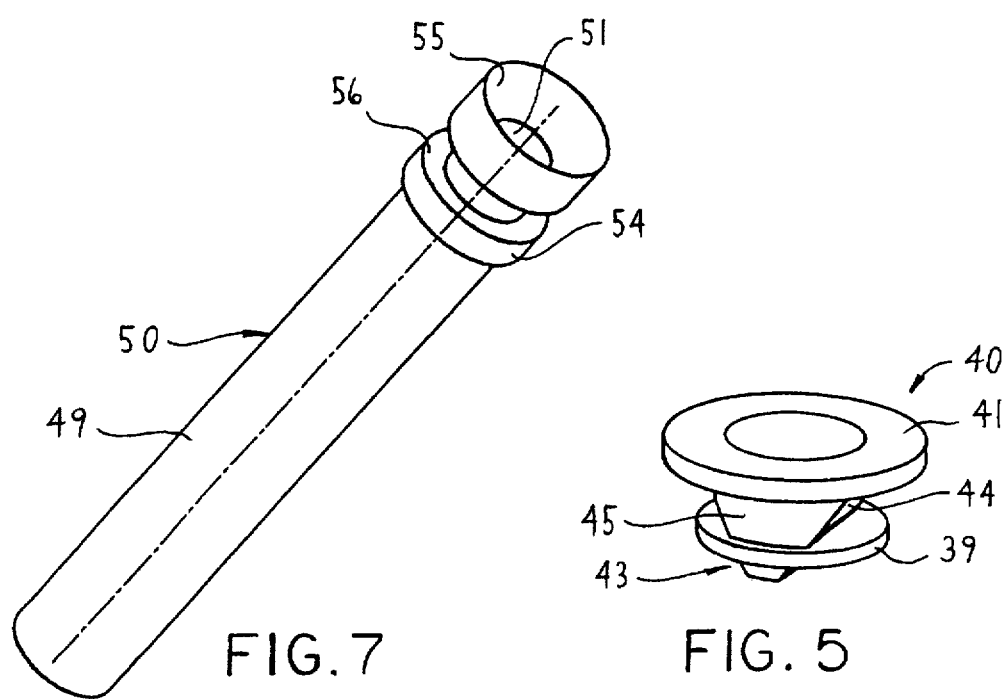

LAPAROSCOPIC SURGICAL Y-TUBE CANNULA

FIELD OF THE INVENTION

This invention relates to a laparoscopic surgical cannula.

BACKGROUND OF THE INVENTION

U.S. Pat. No. 4,886,507 shows a Y-connector for angioplasty in which a casing has an elongate main passageway for receiving a dilation catheter longitudinally therethrough and a branch passageway intersecting the main passageway. The angle between the main and the branch passageways is acute and faces proximately (faces the user). The proximal end of the branch passageway is connectable to a fluid valve structure. The proximal end of the main passageway is provided with a membrane having a small hole for receiving a dilation catheter and a Tuohy-Borst valve coaxial with and spaced from the membrane and for receiving the dilation catheter coaxially therethrough.

U.S. Pat. No. 4,655,752 discloses a surgical cannula having a central bore whose proximal end is enlarged radially to receive the seal member with a central hole and a further, axially spaced seal member having a central slit, all for insertion therethrough of a surgical instrument, for example an endoscope in sealed relation therethrough. The proximal end portion of the cannula is formed as an enlarged cup-shaped housing, to provide room for the above mentioned valves therein. The housing has a side extension extending at right angles from the instrument path through the cannula. The side extension has at its free end a pair of flanges disposed in diametrally opposed relation, each with a circularly curved outer surface. A cap with a screw threaded blind hole on one end cooperates with these flanges on the extension to form a screw on cap arrangement. Upon removal of the cap, access can be had to the surgical site through a bore on the extension and the instrument path through the cannula, whereby fluid may be introduced or removed with respect to the surgical site. The apparatus can serve simultaneously as both an instrument cannula and an irrigation cannula so long as the instrument being used is not so large as to close off the main instrument path to fluid flow, i.e., so that fluid can flow through the main instrument path in the space left between the instrument and the walls of such path.

U.S. Pat. No. 5,201,714 discloses a cannula for laparoscopic surgery comprising a housing and an elongated tube extending distally from the housing so that laparoscopic instruments can be passed through the housing and elongated tube into the abdominal cavity of a patient. The housing includes valve structure to close the proximal end of the passage whether or not a laparoscopic instrument is present in the cannula. A gas valve extends at right angles to the tube, at a location below the housing to admit gas through the tube into the abdominal cavity for insufflation of the abdomen. The valve structure in the housing is intended to prevent escape of such gas from the abdomen therepast, either with or without an instrument inserted down through the housing and tube.

However, none of these prior patents discloses a laparoscopy cannula having the structure and advantages of the present invention.

Accordingly, the objects and purposes of this invention include provision of a laparoscopic cannula in which a surgeon can simultaneously with one hand manipulate a laparoscopic instrument extending through a main passage of the inventive cannula into a surgical site and with the other hand manipulate a suction flow and irrigation flow with respect to the surgical site through the passage in which the laparoscopic instrument is moveable; and in which the surgeon can also maintain the position of the inventive cannula with respect to the patient by moving or maintaining the position of the suction irrigation handpiece.

SUMMARY OF THE INVENTION

An embodiment of the invention includes a laparoscopy cannula having an acutely angled suction irrigation branch, incorporating a suction irrigation fluid seal which is accessible for replacement and a cooperating rotatable and axially slidable coupling having an internal portion for connection to and support of a suction irrigation handpiece.

Further objects and purposes of the invention will be apparent to persons of ordinary skill in this art upon reading the following description and inspecting the accompanying drawings.

BRIEF DESCRIPTION OF THE DRAWINGS

FIG. 1 is a pictorial view of an apparatus embodying the invention.

FIG. 2 is a partially broken elevational view of the FIG. 1 apparatus.

FIG. 3B is a fragmentary elevational view generally similar to FIG. 3 but with the cap on the fitting body removed and the coupling retracted along the angled tubular arm for access to the O-ring seal on the arm.

FIG. 4 is a sectional view substantially taken on line 4—4 of FIG. 2.

FIG. 5 is a pictorial view of the FIG. 3 valve.

FIG. 6 is a central cross sectional view, somewhat enlarged in scale, of the FIG. 5 valve.

FIG. 7 is an enlarged pictorial view of the tubular arm of FIG. 3.

DETAILED DESCRIPTION

Figure 3:
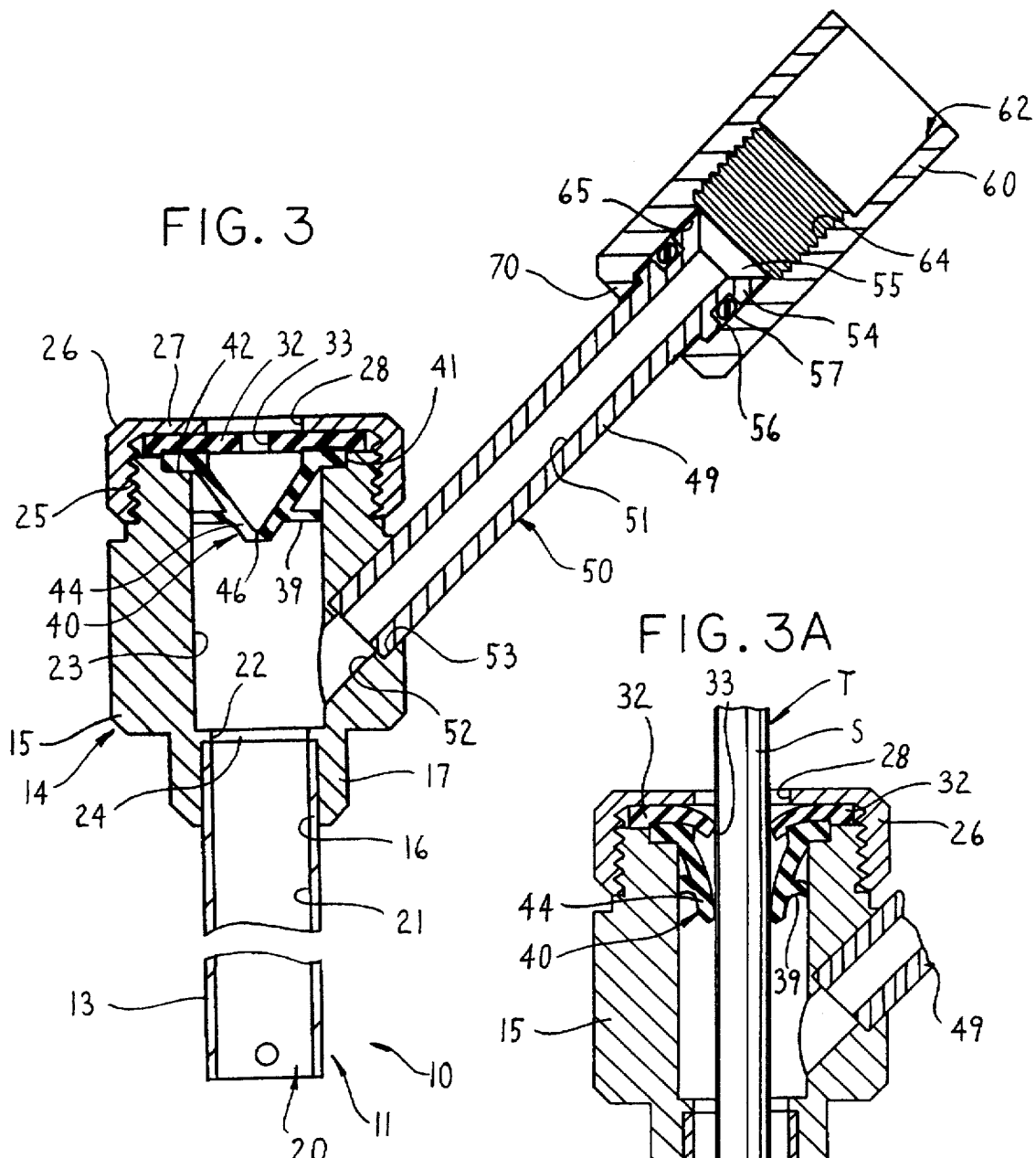
FIG. 3 is an enlarged central cross sectional view of the upper portion of the FIG. 2 apparatus.

A laparoscopic surgical cannula 10 (FIGS. 1–3) embodying the invention comprises a generally Y-shaped member 11 including an elongate tubular stem 12. The stem 12 in turn comprises a distal elongate tube 13 for insertion into a laparoscopic surgical site SS (FIG. 1) and an annular proximal fitting 14 coaxially fixed to the proximal (upper in FIGS. 1–3) end thereof.

In the preferred embodiment shown, the fitting 14 comprises an annular body 15 (FIG. 3). The proximal (upper in FIG. 3) end of the elongate tube 13 seats in a coaxial downward opening recess 16 in a reduced diameter bottom part, or coaxial depending spigot 17, at the bottom of the body 15. In the preferred embodiment shown, the elongate tube 13 and body 15 are preferably of surgical grade stainless steel and are fixed together in a fluid tight manner by any convenient means such as silver soldering. The annular body 15 and elongate tube 13 together define a coaxial through passage 20 for insertion of laparoscopic surgical tools sequentially therethrough from the proximal end (upper end in FIG. 1 and 8 therethrough to the surgical site SS). The through passage 20 includes coaxial portions 21, 22 and 23 (FIG. 3) in the elongate tube 13, an inwardly directed annular flange 24, and the upper portion of the body 15. The inwardly directed annular flange 24 provides an upper end stop locating the elongate tube 13 axially in the bottom side of the body 15 and thus separates the portion 23 of the through passage 20 from the depending tube 13. The portion 23 of the through passage 20 forms a chamber in the upper part of the body 15, which chamber opens through the top thereof. In the embodiment shown, the diameter of the chamber 23 slightly exceeds the inside diameter of the through passage portions 22 and 21.

As seen in FIG. 3, the upper end of the body 15 is externally threaded at 25. An annular, inverted cup-shaped cap 26 is internally threaded to thread onto the upper end portion 25 of the body 15. The cap 26 has an end wall 27 which overlies the upper end of the body 15 and has a central hole 28 therethrough.

A resilient annular plate-like wiper seal 32 rests atop the body 15 under the end wall 27 of the cap 26. The wiper seal 32 has a central hole 33 of substantially smaller diameter than the hole 28 in the cap end wall 27 and than the passage 20, for snugly gripping the shank S (FIG. 3A) of a laparoscopic surgical tool T so as to stretch and sealingly but slidably grip such shank S during its insertion into and retraction from the annular body 15 and tube 13.

A normally closed valve 40 (FIGS. 3, 3A, 5 and 6), here of duck-bill type, is preferably molded out of a suitable resilient material. The valve 40 comprises a radially outward extending rim 41 at the proximal end of the valve, which rim is preferably seated in a shallow recess 42 in the top of the body 15. The rim 41 and recess 42 are preferably of outside diameter less than the outside diameter of the wiper seal 32 and the relaxed axial thickness of the valve rim 41 is preferably slightly greater than the axial depth of the recess 42. Thus, threaded tightening of the cap 26 on the top of the body 15 causes the cap end wall 27 to firmly axially clamp and slightly crush the wiper seal 32 and valve rim 41 fixedly against the top portion of the body 15, so as to positively coaxially locate the wiper seal 32 and valve 40 at the upper end of the through passage portion 23 in the body 15. While the disclosed threaded connection of cap 26 to body 15 is preferred, other means for such connection are contemplated to the extent capable of the mentioned clamping the wiper seal 32 and valve rim 41 fixedly against the body 15.

Figure 6A:
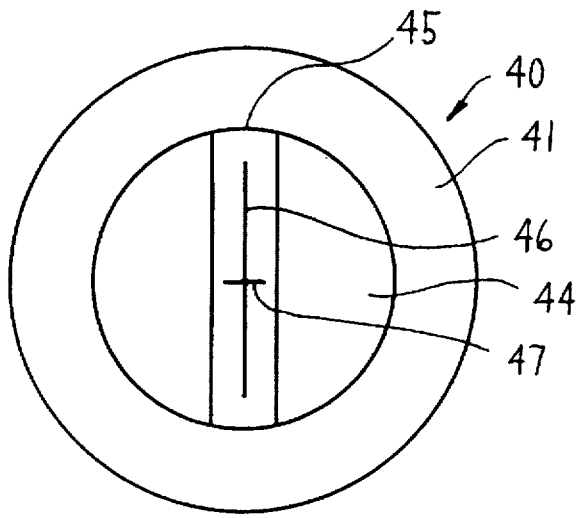
FIG. 6A is a bottom view of the FIG. 6 valve.

The resilient valve 40 further includes a downward tapering integral resilient skirt 43 comprising a diametrally opposed pair of resilient, convergent leaves 44 circumferentially joined by skirt portions 45. The bottom edges of the leaves 44 meet in a normally closed diametral slit 46 (FIG. 6A). In the embodiment shown, the diametral slit 46 has a short central perpendicular cross cut at 47 to facilitate opening of the slit to promote insertion of a laparoscopic surgical tool T therethrough.

The resilient valve 40 preferably further includes a resiliently flexible, flange-like, annular, reinforcing disk 39 circumferentially surrounding and extending radially out from the leaves 44 and spaced axially between the rim 41 and diametral slit 46 for helping press the leaves 44 together at the slit 46 to help close the valve 40, the reinforcing disk 39 having an outer perimeter preferably radially backed by the inner surface of the through passage 23 of the fitting 14. The disk 39 acts like a spring to more strongly return the resilient leaves 44 to their closed position. The disk 39 is here coaxial with the rim 41 of the valve 40.

The valve 40 is preferably molded in one piece of a suitable elastomeric material e.g. surgical grade silicone rubber.

The Y-shaped tubular member 11 (FIGS. 1–3) further includes a tubular arm 50. The tubular arm 50 is fixed to the peripheral wall of the body 15 between the cap 26 and spigot 17 and extends proximally at an acute angle, preferably about 45° to the length axis of the body 15 and elongate tube 13. The tubular arm 50 is substantially shorter than the elongate tube 13 but longer than the fitting 15. The tubular arm 50 has a coaxial through passage 51 in distal end communication with a port 52 in the peripheral wall of the body 15, which port 52 communicates with the lower portion of the chamber 23. In the preferred embodiment shown, the tubular arm 50 is of stainless steel, similar to the preferred material of the body 15 and is received in a radially and distally opening recess 53 of the port 52. In one unit constructed according to the invention, the distal end of the tubular arm 50 was fixed by silver soldering within the recess 53. However, it is contemplated that other means may be utilized to establish the fixed connection, for example, by use of a threaded connection (not shown).

The tubular arm 50 comprises an elongate hollow shank 49 and a radially enlarged substantially cylindrical head 54 at the proximal end of the shank. The tubular arm 50 is of circular outside cross section. The proximal end of the head 54 has a frustoconical recess 55 which coaxially tapers into the proximal end of the through passage 51. The head 54 further includes an annular groove 56 (FIGS. 3 and 7) in the periphery thereof for receiving an annular seal member, preferably a conventional O-ring.

A coupling 60 is in the form of an axially elongate hollow sleeve rotatably and axially slidably sleeved over the tubular arm 50.

The coupling 60 preferably has a textured outer peripheral surface for easy gripping and twisting by the human hand, such surface being here provided by a circumferentially spaced series of longitudinal grooves 51 (FIG. 2).

The coupling sleeve 60 has a coaxial through opening generally indicated at 62 and comprised of four successively radially outwardly stepped portions 63–66 arranged between the proximal and distal ends, respectively, thereof. More particularly, the opening portion 66 at the distal end of the coupling 60 is of least diameter and short axial length. Such opening portion 66 is bounded by a radially inward extending annular flange (FIG. 3) which snugly surrounds, but is axially and rotatably movable on, the shank 49 of the arm 50 and acts to axially oppose the fitting body 15 and head 54, so as to positively trap the coupling 60, and hold same captive, on the arm 50.

Immediately proximal beyond the annular flange 70 is the substantially cylindrical opening portion 65 (FIGS. 3 and 3B) in which the head 54 is received in clearance relation, for axial and rotation motion of the coupling 60 on the head 54. The opening portion 65 bears with its internal peripheral wall against the O-ring 57 to seal against axial fluid flow therepast. Proceeding proximally, the next cylindrical opening portion 64 is internally threaded for threadedly receiving a male threaded end 71 of elongate hollow tip 72 of a suitable suction/irrigation handpiece 73 schematically indicated in FIGS. 1 and 8. While the mentioned threaded connection at 64, 71 is preferred, other positive connections, particularly those involving a twisting of the coupling 60 to connect and disconnect, are contemplated. The handpiece 73 may handle both the suction and irrigation functions or only one such function, as desired.

As schematically shown in FIG. 1, the handpiece 73 preferably includes suitable manually actuable valves VL and VS for controlling flow between the hollow tip 72 and a conventional irrigation liquid source IL and suction source SU, respectively. The valves VL and VS are actuable to turn on and off the flow therethrough and, if desired, may be adjustable to operate also in a partially open condition. The valves VL and VS may be actuated in any desired manner, for example by spring returned push buttons PL and PS respectively.

Figure 9:
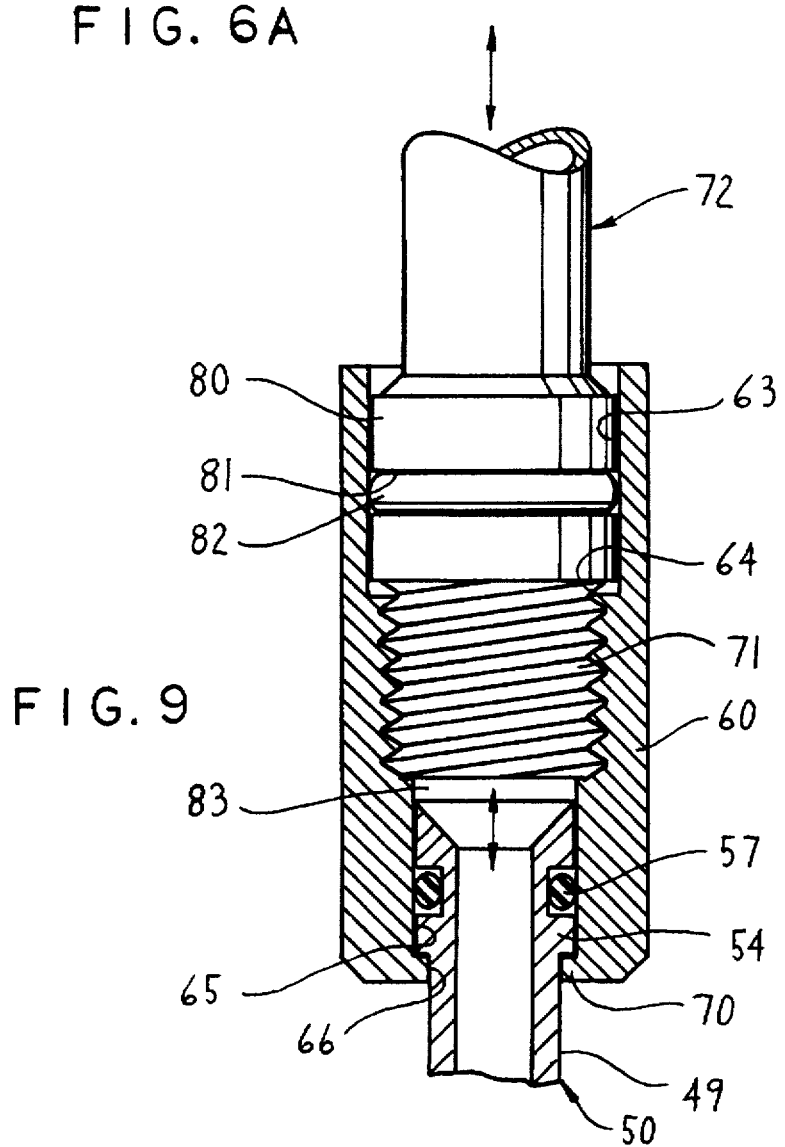
FIG. 9 is a central cross sectional view similar to FIG. 3 of the inventive cannula and the suction irrigation handpiece fixed thereto.

The proximal portion 63 of the through opening 62 of the coupling 60 is, in the embodiment shown in FIG. 6A, provided with a cylindrical peripheral wall stopped radially outward from the threaded internal wall of opening portion 64. The proximal opening portion 63 is sized for receiving a radially enlarged, substantially cylindrical, coaxial boss 80 of the handpiece tip 72 snugly but slidably therein. The boss 80 is preferably provided with an annular groove 81 in turn provided with a resilient annular seal member, for example, an O-ring 82. The O-ring 82 is adapted to seal against the peripheral wall of the opening portion 63. In this way, suction or irrigation flow between the hollow shank 49 of the tubular arm 50 and the suction irrigation handpiece tip 72 is prevented from leaking both distally and proximally from the coupling 60 by the O-rings 57 and 82 respectively. At the same time, even with the handpiece hollow tip 72 threaded tightly into the coupling 60, the coupling 60, and with it the handpiece 2, can rotate relatively freely on the tubular arm 50 without risk of leakage axially outward past the O-rings 57 and 82. To facilitate rotation of the coupling 60 on the tubular arm 50, some axial clearance is preferably left between the head 54 and the flange 70 or free end of the threaded end 71 of the handpiece tip 72. An axial clearance of 0.005 to 0.010 inch is sufficient for such axial clearance, although in FIG. 9 such axial clearance is shown exaggerated at 83.

The laparoscopic surgical cannula 10 embodying the invention may be reusable. Where intended to be reusable, the nonresilient parts thereof, namely the elongate tube 13, body 15, cap 26, and tubular arm 50 are preferably constructed of stainless steel.

It may be desirable to replace, after extended use, resilient parts such as the wiper 32, valve 40 and O-ring 57. The wiper seal 32 and the valve 40 are readily replaceable by removal of the cap 26. The O-ring 57 is replaceable by displacing the collar 60 distally along the hollow shank 49 toward the body 15. The length of the shank 49 and collar 60 are set so that the O-ring 57 is exposed with the collar 60 in its position closest to the body 15, as shown in FIG. 3B. In the particular embodiment shown in FIG. 3B, the cap 26 is removed from the threads 25 on the body 15 to allow the collar 60 to be close enough to the body 15 as to fully expose the O-ring 57. Thus exposed, the O-ring 57 can be removed by any convenient means, for example by prying it off or cutting it off. A new O-ring can readily be slipped over the proximal end of the head 54 and into the groove 56.

During assembly of the laparoscopic surgical cannula 10, the collar 60 is telescoped on the tubular arm 50 before the distal end of the tubular arm 50 is fixed to the body 15, thereby capturing axially the flange 70 of the collar 60 between the body 15 and the head 54 of the tubular arm 50.

To use the laparoscopic surgical cannula 10, the suction/irrigation (either or both) handpiece 73 is easily fixed to the cannula 10 by inserting the male threaded end 71 of the hollow handpiece tip 72 into the female threaded portion 64 of the collar 60, and rotating the collar 60 in the on-threading rotational direction, with respect to both the laparoscopic surgical cannula 10 and handpiece 73. More particularly, during such threading, neither the laparoscopic surgical handpiece 10 nor the suction irrigation handpiece 73 need rotate, or even move. This is helpful since it avoids a cumbersome rotation of the elongated Y-shaped member 11 and also avoids twisting of the usual flexible hoses connecting the handpiece 73 to the usual irrigation liquid and suction sources.

Figure 3A:
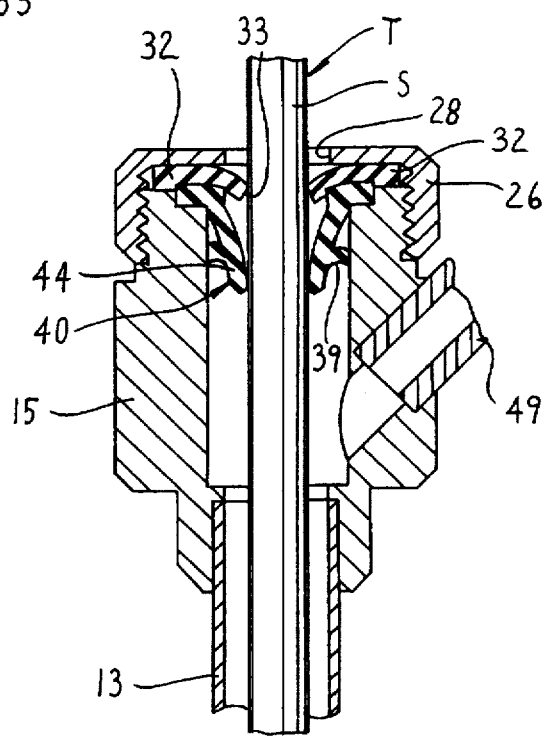
FIG. 3A is a view similar to FIG. 3 but with an instrument inserted longitudinally into the proximal end portion of the apparatus.

After the suction irrigation handpiece 73 is connected to the laparoscopic surgical cannula 10, the distal end of the elongate tube 13 (FIG. 1) can be inserted into a previously installed conventional laparoscopic outer cannula OC (FIGS. 1 and 8) and be lead thereby into the surgical site SS in the patient P. Thereafter a suitable laparoscopic surgical tool (e.g. a cutter, dissector, scissors, etc.), indicated at T in FIGS. 1 and 8, can be inserted down through the cap 26 (FIG. 3A) and wiper seal 32, valve 40, portions 21, 22 and 23 of the through passage 20 (as shown in FIG. 3A) and then finally into the surgical site SS as seen in FIG. 8.

Figure 8:
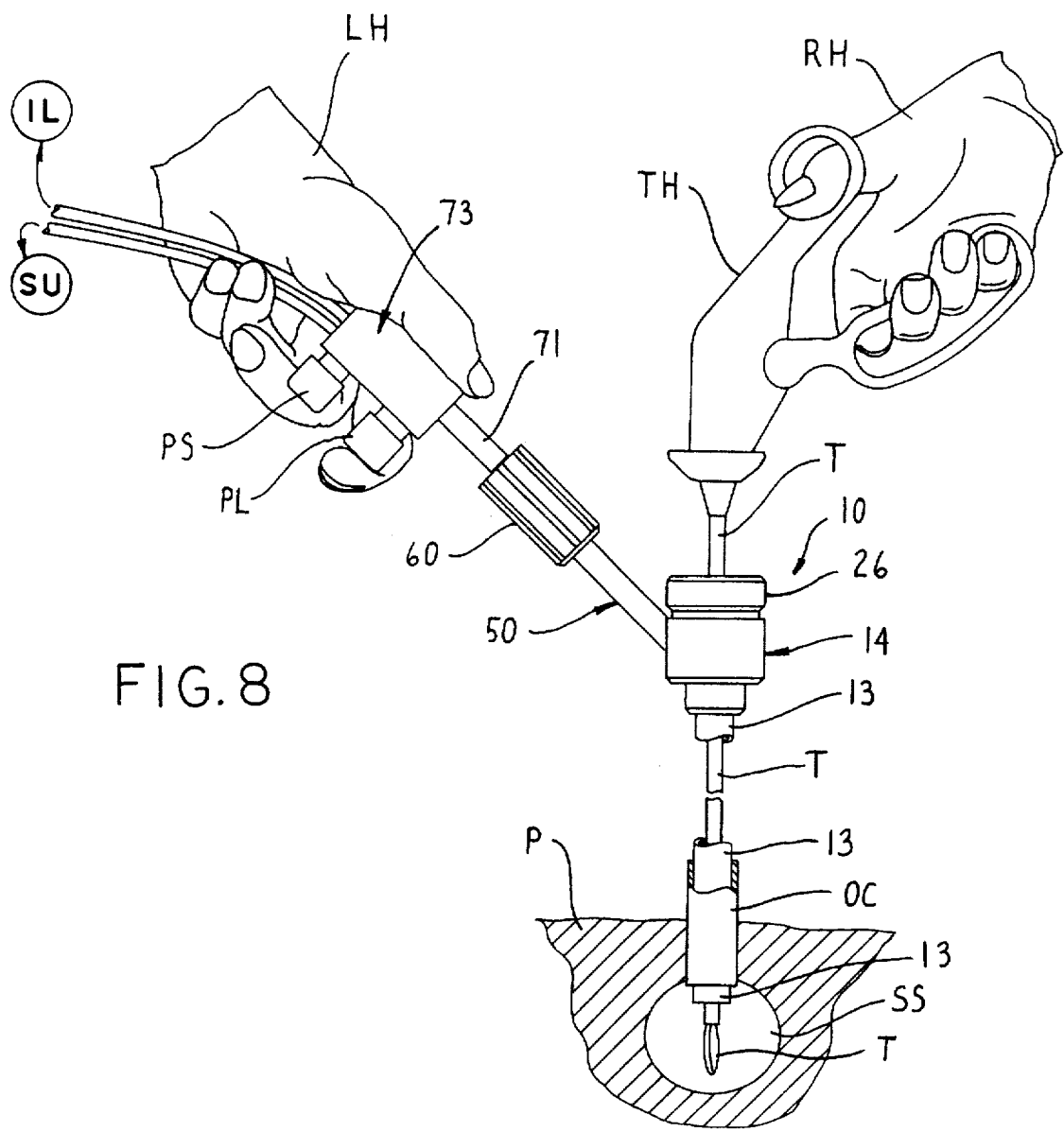
FIG. 8 is a somewhat schematic, partially broken, fragmentary, elevational view of the FIG. 1 apparatus, showing it in association with a laparoscopic tool, a suction irrigation handpiece, a surrounding lead-in cannula, and a surgical site in a patient, and showing the handling of the apparatus by the two hands of a surgeon.

Depending on the type of laparoscopic surgical tool T used, the proximal end thereof may be supported by some sort of a hand engageable and/or actuable handpiece, a suitable example of which is generally indicated at TH in FIG. 8. By way of example only, the tool handpiece TH in FIG. 8 is suitable for hand actuating a scissors-like tool T.

Carrying out laparoscopic surgery, it will be understood that other cannulae (not shown) will normally enter the surgical site to provide for lighting, camera or direct eye vision, etc. in a conventional manner.

In carrying out a surgical procedure, the surgeon can conveniently grip the suction irrigation handpiece 73 in one hand LH and the tool handpiece TH in the other hand RH. The surgeon can then directly control suction and irrigation flow and tool operation, without need for the usual human assistant in charge of suction and irrigation flow. In this way, the surgeon can instantaneously control suction and irrigation flow, without the delay previously needed to formulate and vocalize instructions to a human assistant and wait for that assistant to assimilate the instructions and act thereon, occasionally with error requiring additional delay for correction.

In addition, as can be seen at FIG. 8, by reason of the two-hand connection to the laparoscopic surgical cannula 10, provided on one side by the suction irrigation handpiece 73 and on the other side by the tool handpiece TH, the surgeon can, in addition to controlling suction and irrigation flow and actuation of the laparoscopic surgical tool T, also use the handpieces 73 and TH to make the laparoscopic surgical cannula 10 move up and down within the outer cannula OC, pivot parallel to the plane of the paper in FIG. 8, pivot in a direction transverse to the plane of the paper in FIG. 8 and twist about the axis of the tube 13 in FIG. 8. Thus, while actuating the suction end or irrigation liquid with hand LH and actuating or raising or lowering the tool T with hand RH, the surgeon can simultaneously change the effective angle of attack of the laparoscopic surgical cannula 10 with respect to the patient as well as twist the apparatus around the upstanding central axis of the outer cannula OC. The generally bicycle hand grip stance of the hands LH and RH in FIG. 8 provides sure and finally incremental adjustments in the attitude and insertion depth of the tool T.

In addition, the ability of the hand LH to rotate with respect to the cannula 10, for example while rocking the laparoscopic surgical cannula 10 into and out of the page in FIG. 8, allows the hand LH supporting the suction irrigation handpiece 73 to maintain a comfortable orientation with respect to the body of the surgeon. More particularly, as the surgeon rocks the laparoscopic surgical cannula 10 into and out of the plane of the page in FIG. 8, the collar 60, and with it the handpiece 73, can pivot around the length axis of the tubular arm 50, allowing the surgeon to maintain the most comfortable wrist angle (hand to forearm angle), rather than having to twist his wrist as would be the case if the suction irrigation handpiece 73 coupling were not rotatable with the respect to the tubular arm 50.

To avoid any tendency of the valve leaves 44 to stick to the tool T as it is being withdrawn upwardly (proximally) from the cannula 10, at least the leaves 44 are preferably impregnated with a suitable low friction agent, such as PTFE (tradename Teflon) or more particularly polytetrafluoroethylene.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A laparoscopic surgical cannula, comprising:
    a generally Y shaped tubular member comprising an elongate tubular stem having a distal elongate tube insertable in a laparoscopic surgical wound and a compact annular proximal fitting on said elongate tube for telescopingly receiving therein a laparoscopic surgical tool, said elongate tube having proximal and distal ends, said elongate tubular stem having a through passage extending longitudinally through said fitting and elongate tube and open at opposite ends of stem for guiding an elongate laparoscopic surgical tool distally therethrough to a surgical site at a distal end of said stem, said Y shaped tubular member further comprising a tubular arm fixed to said proximal fitting at a location spaced from the ends thereof and extending from said fitting radially and proximately at an acute angle, said tubular arm having a through passage having an open proximal end and a distal end opening into and communicating with said passage of said elongate tubular stem for providing a path for fluids between the proximal end of said tubular arm and a distal end of said elongate tube, said path for fluids extending the length of said tubular stem and through a distal portion of said elongate tube to said distal end of said elongate tube;
    a coupling on the proximal end of said tubular arm for connection to a fluid transfer device;
    a normally closed valve on said fitting for preventing escape of fluid under pressure in the surgical site proximally past said fitting, said valve opening in response to insertion of a laparoscopic surgical tool through said fitting toward said distal end of said elongate tube, such that the same surgical wound in the patient serves for both tool insertion and fluid communication, thereby avoiding need for separate incisions for a tool and fluid communication;
    said compact proximal fitting including
        (1) an annular central body including a peripheral wall surrounding coaxially a through chamber, a port through said peripheral wall from said chamber to outside said body, said proximal fitting being compact with said body being externally cylindrical and of diameter exceeding length, said port being angled proximately and radially outward from said through chamber and having a coaxial recess opening out through said peripheral wall, said port being at the distal end of said chamber, said recess being at said proximal end of said body, and
        (2) a reduced diameter annular distal flange extending distally coaxially from said body and having a distal opening recess coaxial with and axially continuing said chamber of said body and fixedly receiving the proximal end of said elongate tube, said distal flange being axially shorter than said body, and
        (3) a reduced diameter annular proximal flange extending proximately coaxially from said body and axially continuing said chamber of said body and having external threads and being substantially equal in axial length to said distal flange;
    an annular cap having a coaxial through hole whose distal end is radially enlarged by a coaxial distal central recess, said annular cap being cup-shaped and having an annular proximal end wall coaxially pierced by said through hole, said cap having a distal peripheral wall bounding said distal recess and having internal threads threadedly engaging said external threads on said proximal annular flange of said proximal fitting;
    a resilient annular washer defining a wiper seal;
    said normally closed valve comprising an annular washer-like rim at the proximal end of said valve and a skirt extending distally therefrom, said cap proximal end wall and resilient annular washer and annular washer-like rim and proximal fitting annular proximal flange together forming a contiguous coaxial stack, with said washer and rim axially pressed sealingly against and between said cap proximal end wall and the opposed proximal end of said proximal fitting annular proximal flange.

2. The apparatus of claim 1 in which said coupling is rotatable on said tubular arm and includes means responsive to twisting between said coupling and a mating part of a fluid transfer device for effecting connection therebetween.

3. The apparatus of claim 1 in which said valve closure is normally closed and is inserted into said through passage of said body and extends distally from said cap and comprises circumferentially connected resilient leaves with edges normally abutting to form a closed slit openable by insertion of a laparoscopic surgical tool axially therethrough.

4. The apparatus of claim 3 in which said valve is of duck-bill type having at least two said leaves, said valve having a flange structure protruding laterally from said resilient leaves and coaxial with said annular rim to help return said resilient leaves to a closed position in a spring-like manner.

5. The apparatus of claim 1 in which said tubular arm extends from said annular fitting.

6. The apparatus of claim 5 in which said tubular arm connects with said body at a location distal of said valve.

7. The apparatus of claim 1 in which said valve is a duck-bill valve comprising a diametrally opposed pair of resilient leaves circumferentially joined and having a normally closed diametral slit at the distal end of said leaves, said valve further comprising a radially outward extending rim at substantially the proximal end of said valve for fixed clamping axially with respect to said fitting, the opposed surfaces of said valve leaves being relatively slippery to avoid eversion of said leaves as a tool is slid proximally therebetween.

8. The apparatus of claim 1 in which said fitting through chamber has a proximal end and a recess in said proximal end communicating with said through opening in said fitting, said valve having leaves extending distally into said through opening, said rim being received in said recess, said wiper seal abutting the proximal end of said body radially outboard of said recess, said cap axially pressing said wiper seal against the proximal end of said body and said rim of said valve into said recess at respective radially outer and inner parts of said wiper seal.

9. The apparatus of claim 1 in which said coupling on said arm comprises an axially elongate sleeve rotatably and axially slidable on said arm, said arm comprising a hollow shank extending from said fitting and carrying a hollow radially enlarged proximal head, said sleeve having a radially inward extending annular flange surrounding and axially and rotatably moveable on said arm shank between said fitting and arm head, axial interference between said arm head and sleeve flange maintaining said coupling captive on said tubular arm.

10. The apparatus of claim 9 in which said sleeve has a central through opening extending proximately from said inward extending radial flange and comprising a head receiving chamber and a threaded bore for threadedly engaging a fluid transfer device.

11. The apparatus of claim 10 in which said head has an annular recess and a seal ring therein for sealing against the interior peripheral wall of said head receiving chamber of said sleeve.

12. The apparatus of claim 9 in which said sleeve has a proximal recess, said head receiving chamber and threaded bore and proximal guide recess being of sequentially larger inside diameters.

13. The apparatus of claim 9 in which the interior of said sleeve has a radially outward flared, funnel-like, proximal end.

14. A laparoscopic surgical cannula, comprising:

a generally Y shaped tubular member comprising an elongate tubular stem having a distal elongate tube insertable in a laparoscopic surgical wound and an annular proximal fitting on said elongate tube for telescopingly receiving therein a laparoscopic surgical tool, said elongate tube having proximal and distal ends, said elongate tubular stem having a through passage extending longitudinally through said fitting and elongate tube and open at opposite ends of said stem for guiding an elongate laparoscopic surgical tool distally therethrough to a surgical site at a distal end of said stem, said Y shaped tubular member further comprising a tubular arm fixed to said proximal fitting at a location spaced from the ends thereof and extending from said fitting radially and proximately at an acute angle, said tubular arm having a through passage having an open proximal end and a distal end opening into and communicating with said passage of said elongate tubular stem for providing a path for fluids between the proximal end of said tubular arm and a distal end of said elongate tube, said path for fluids extending the length of said tubular stem and through a distal portion of said elongate tube to said distal end of said elongate tube;

a coupling on the proximal end of said tubular arm for connection to a fluid transfer device;

a normally closed valve on said fitting for preventing escape of fluid under pressure in the surgical site proximally past said fitting, said valve having a closure which opens in response to insertion of a laparoscopic surgical tool through said fitting toward said distal end of said elongate tube, such that the same surgical wound in the patient serves for both tool insertion and fluid communication, thereby avoiding need for separate incisions for a tool and fluid communication;

said valve being a one-piece duckbill type seal of resilient material and integrally comprising (1) a first radially protruding annular washer-like portion defining a rim at the proximal end of said valve, (2) a generally conical skirt tapered distally and coaxially from said rim to a narrowed distal end spaced distally from said rim, said skirt comprising circumferentially connected resilient leaves with edges normally abutting to form a closed slit openable by insertion of a laparoscopic surgical tool axially therethrough, said valve having at least two said leaves, (3) a second radially protruding annular washer-like portion defining a flange structure surrounding a portion of said skirt spaced between said rim and the distal end of said skirt, said second washer-like portion being of outside diameter less than said first washer-like portion, said second washer-like portion being of outside diameter less than the inside diameter of said through passage in said fitting and being radially spaced from the interior peripheral wall of said fitting, said flange structure protruding laterally from said resilient leaves and coaxial with said annular rim to help return said resilient leaves to a closed position in a spring-like manner.

15. The apparatus of claim 14 in which said fitting includes an annular body fixed on the proximal end of said elongate tube and having a through passage continuing said through passage of said elongate tube for insertion of a surgical tool therethrough, a resilient annular plate-like wiper seal for generally sealed insertion of a surgical tool axially therethrough, and an annular cap fixed on said body for retaining said wiper seal and valve with respect to said body.

16. The apparatus of claim 15 in which said wiper seal and valve rim are axially sandwiched between said cap and body.

17. The apparatus of claim 15 in which said cap is releasably fixed on said body at a proximal end of said body.

* * * * *

UNITED STATES PATENT AND TRADEMARK OFFICE
CERTIFICATE OF CORRECTION

PATENT NO. : 5,613,954
DATED : March 25, 1997
INVENTOR(S) : Charles L. NELSON, et al It is certified that error appears in the above-indentified patent and that said Letters Patent is hereby corrected as shown below:

Column 8, line 49; after "valve" insert ---has a---.
after "closure" insert ---which---.
line 50; replace "passage" with ---chamber---.
Column 9, line 37; replace "9" with ---10---.

Signed and Sealed this

Second Day of September, 1997

Attest:

BRUCE LEHMAN

Attesting Officer

Commissioner of Patents and Trademarks